United States Patent
Bolosan

(10) Patent No.: US 10,314,632 B2
(45) Date of Patent: Jun. 11, 2019

(54) SURGICAL SYSTEM AND METHODS OF USE

(71) Applicant: Medtronic Holding Company Sàrl, Tolochenaz (CH)

(72) Inventor: Samuel Bolosan, San Jose, CA (US)

(73) Assignee: Medtronic Holding Company Sárl, Tolochenaz (CH)

( * ) Notice: Subject to any disclaimer, the term of this patent is extended or adjusted under 35 U.S.C. 154(b) by 421 days.

(21) Appl. No.: 15/288,570

(22) Filed: Oct. 7, 2016

(65) Prior Publication Data

US 2018/0098804 A1    Apr. 12, 2018

(51) Int. Cl.
*A61B 17/88*    (2006.01)
*A61B 17/00*    (2006.01)

(52) U.S. Cl.
CPC ...... *A61B 17/8819* (2013.01); *A61B 17/8808* (2013.01); *A61B 17/8855* (2013.01); *A61B 2017/00867* (2013.01)

(58) Field of Classification Search
CPC .......... A61B 17/8855; A61M 25/0125; A61M 25/10
See application file for complete search history.

(56) References Cited

U.S. PATENT DOCUMENTS

| | | | |
|---|---|---|---|
| 6,632,235 B2 | 10/2003 | Weikel et al. | |
| 6,719,773 B1 * | 4/2004 | Boucher | A61B 17/68 606/192 |
| 6,923,813 B2 | 8/2005 | Phillips et al. | |
| 7,544,196 B2 | 6/2009 | Bagga et al. | |
| 7,621,952 B2 | 11/2009 | Truckai et al. | |
| 7,736,292 B2 | 6/2010 | Hermann et al. | |
| 7,749,228 B2 | 7/2010 | Lieberman | |
| 7,963,942 B2 | 6/2011 | Chen | |
| 7,985,228 B2 * | 7/2011 | Phan | A61B 17/8855 606/90 |
| 8,142,463 B2 | 3/2012 | Arcenio et al. | |
| 8,262,609 B2 | 9/2012 | Sapida et al. | |

(Continued)

FOREIGN PATENT DOCUMENTS

CN    201168076    12/2008
CN    201855299    6/2011

(Continued)

OTHER PUBLICATIONS

European Search Report for Application EP17187891, the counterpart application, dated Feb. 19, 2018, 10 pages.

*Primary Examiner* — Andrew Yang

(57) ABSTRACT

A surgical system is provided that includes a body extending along a longitudinal axis. A first member is rotatably positioned within the body and includes a first threaded surface. A second member is positioned within the body and includes a second threaded surface that engages the first threaded surface. The second member is non-rotatable relative to the body. A third member is positioned within the first member. An inflatable bone tamp includes an outer shaft coupled to the body, a balloon coupled to the outer shaft and an inner shaft coupled to the third member and the balloon. The first member is rotatable relative to the body to translate the third member along the longitudinal axis to move the balloon from a first length to a second length. Kits and methods are disclosed.

20 Claims, 16 Drawing Sheets

(56) References Cited

U.S. PATENT DOCUMENTS

| | | |
|---|---|---|
| 8,361,078 B2 | 1/2013 | Beyar et al. |
| 8,366,773 B2 | 2/2013 | Schaller et al. |
| 8,439,878 B2 * | 5/2013 | Bonnette .......... A61B 17/32037 604/165.02 |
| 8,535,327 B2 | 9/2013 | Schaller et al. |
| 8,728,081 B2 | 5/2014 | Lauchner et al. |
| 8,882,836 B2 | 11/2014 | Schaller et al. |
| 8,961,525 B2 | 2/2015 | Donovan |
| 8,979,929 B2 | 3/2015 | Schaller |
| 9,028,464 B2 | 5/2015 | Arthur et al. |
| 9,066,808 B2 | 6/2015 | Schaller |
| 9,089,347 B2 | 7/2015 | Sankaran et al. |
| 9,149,318 B2 | 10/2015 | Druma |
| 9,161,818 B2 | 10/2015 | Arthur et al. |
| 9,173,701 B2 | 11/2015 | Goshayeshgar |
| 9,192,420 B2 | 11/2015 | Druma |
| 9,204,915 B2 | 12/2015 | Arthur et al. |
| 9,211,153 B2 | 12/2015 | Fisher et al. |
| 9,247,980 B2 | 2/2016 | Arthur et al. |
| 9,254,157 B2 | 2/2016 | Mafi et al. |
| 9,295,510 B2 | 3/2016 | Auyoung |
| 9,295,528 B2 | 3/2016 | Arthur et al. |
| 2007/0010845 A1 | 1/2007 | Gong et al. |
| 2009/0024087 A1 | 1/2009 | Kennedy, II et al. |
| 2009/0270893 A1 | 10/2009 | Arcenio |
| 2010/0241178 A1 | 9/2010 | Tilson et al. |
| 2012/0029511 A1 | 2/2012 | Smith et al. |
| 2012/0259355 A1 | 10/2012 | Druma et al. |
| 2013/0018376 A1 | 1/2013 | Yoon et al. |
| 2013/0165942 A1 | 6/2013 | Tan-Malecki |
| 2013/0197563 A1 | 8/2013 | Saab et al. |
| 2013/0238038 A1 | 9/2013 | Auyoung |
| 2014/0214085 A1 | 7/2014 | Druma |
| 2014/0235997 A1 | 8/2014 | Smith et al. |
| 2014/0276572 A1 | 9/2014 | Auyoung |
| 2014/0277211 A1 | 9/2014 | Arthur et al. |

FOREIGN PATENT DOCUMENTS

| | | |
|---|---|---|
| EP | 2702957 A1 | 3/2014 |
| EP | 3305228 A1 | 4/2018 |

* cited by examiner

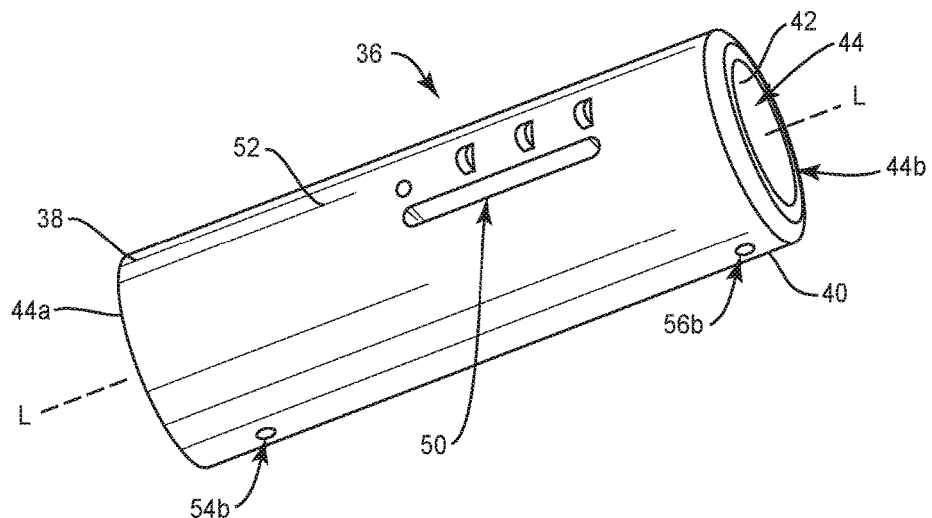
FIG. 4
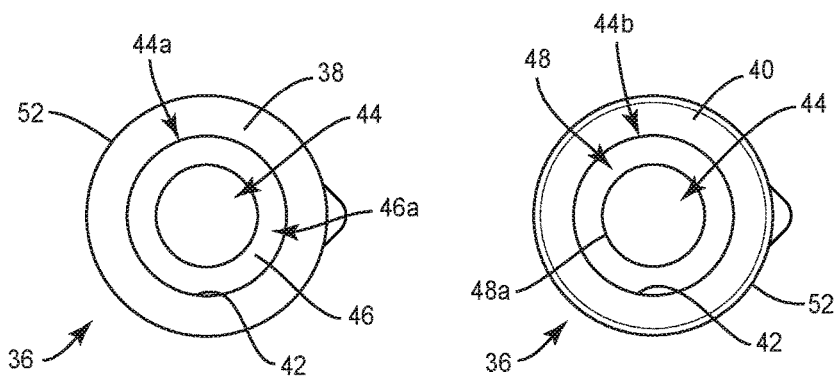
FIG. 5     FIG. 6

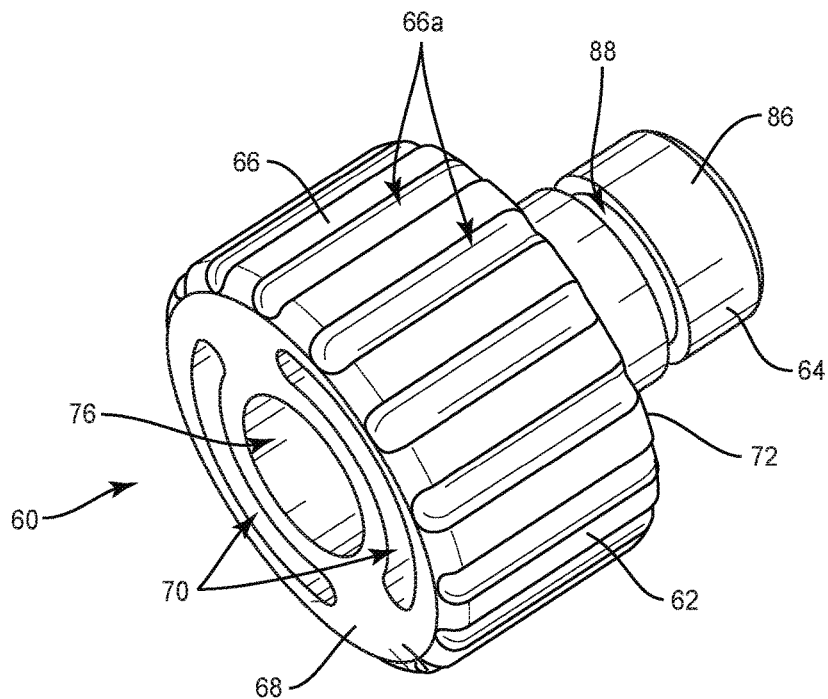
FIG. 9
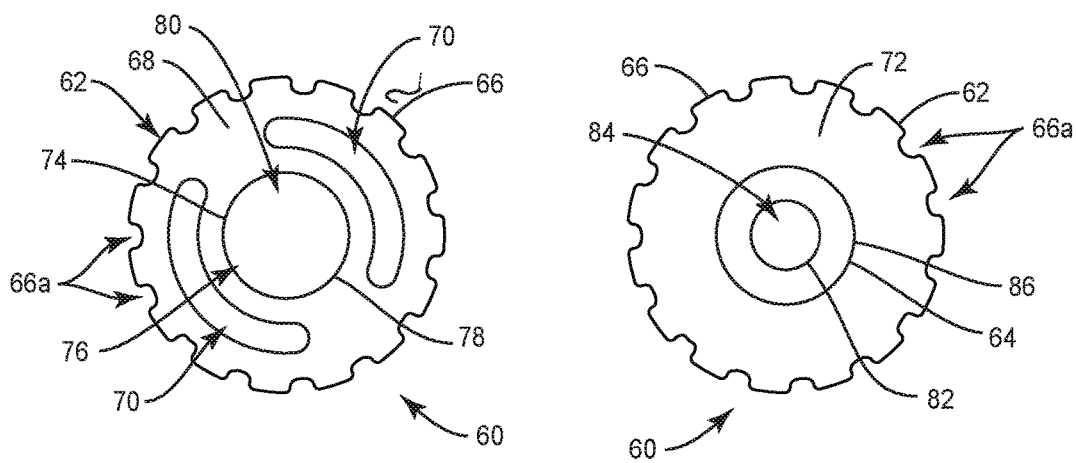
FIG. 10  FIG. 11

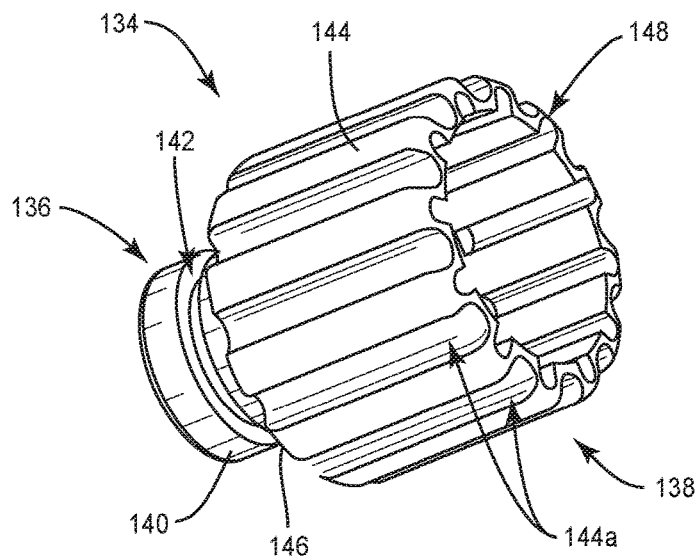
FIG. 18
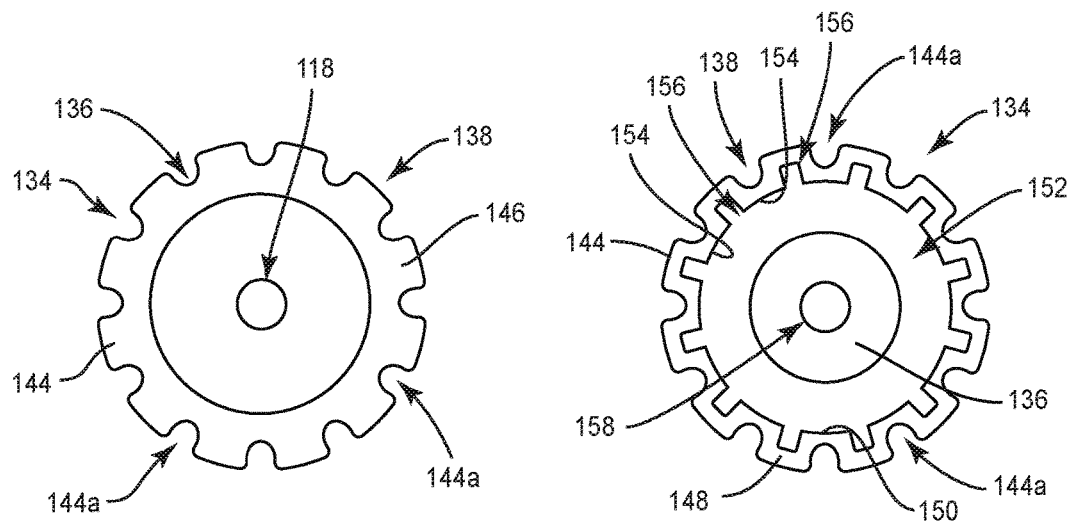
FIG. 19  FIG. 20

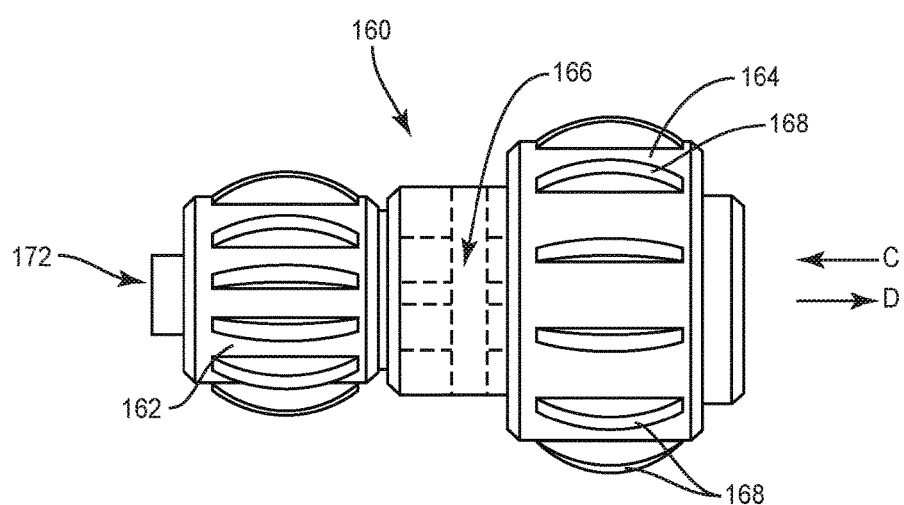
*FIG. 21A*
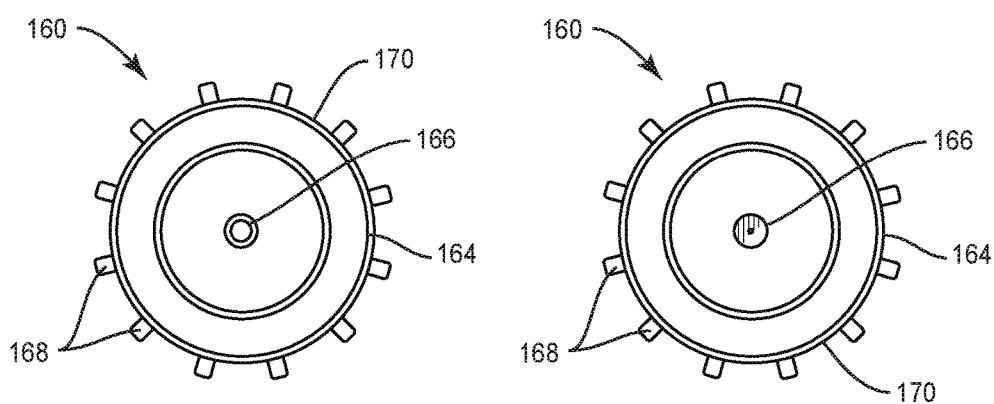
*FIG. 21B*  *FIG. 21C*

SURGICAL SYSTEM AND METHODS OF USE

TECHNICAL FIELD

The present disclosure generally relates to medical devices for the treatment of bone disorders, and more particularly to an inflatable bone tamp withdrawal and longitudinal growth control mechanism.

BACKGROUND

Height loss is commonly associated with spinal fractures, such as, for example, vertebral compression fractures. Spinal fractures affect a large segment of osteoporotic patients. It is estimated that approximately 700,000 spinal fractures occur annually from osteoporosis, for example. Procedures have been developed to treat spinal fractures. One such procedure is kyphoplasty. Kyphoplasty is a minimally invasive procedure that is used to treat spinal fractures, such as, for example, vertebral compression fractures by inserting an inflatable bone tamp inside a fractured vertebral body. The balloon or balloons of the inflatable bone tamp are inflated within the fractured vertebral body such that the cancellous bone of the vertebral body is pushed towards cortical walls of the vertebral body to form a cavity within the vertebral body. The cavity is then at least partially filled with a material, such as, for example, bone cement.

However, conventional inflatable bone tamps lack a means to control the longitudinal expansion of the balloon or balloons. Because longitudinal expansion of the balloon or balloons determine, at least in part, the size of a cavity created by the balloon or balloons, it is thus difficult to control the size of the cavity. That is, the size of the cavity created by the balloon or balloons may be smaller or larger than desired. In instances where the cavity is too small, a second cavity that overlaps the initial cavity may be required to increase the size of the initial cavity. In instances where the cavity is too large, the cavity is filled with more bone cement than is actually needed. Neither situation is desirable, as would be apparent to one of ordinary skill in the art.

Furthermore, conventional inflatable bone tamps often do not allow the profile of the balloon to be reduced sufficiently to prevent or reduce trauma or injury to the patient as the inflatable bone tamp is removed from the patient. That is, the profile of the balloon, even when the balloon is deflated, is too large to prevent trauma or injury to the patient. This disclosure describes improvements over these prior art technologies.

SUMMARY

New systems and methods are provided for the treatment of bone disorders, and more particularly systems and methods for treating spinal disorders, such as, for example, vertebral compression fractures. In some embodiments, the systems comprise a mechanism for an inflatable bone tamp withdrawal and longitudinal growth control.

In one embodiment, a surgical system is provided in accordance with the present disclosure. The surgical system includes a body extending along a longitudinal axis. A first member is rotatably positioned within the body and includes a first threaded surface. A second member is positioned within the body and includes a second threaded surface that engages the first threaded surface. The second member is non-rotatable relative to the body. A third member is positioned within the first member. An inflatable bone tamp includes an outer shaft coupled to the body, a balloon coupled to the outer shaft and an inner shaft coupled to the third member and the balloon. The first member is rotatable relative to the body to translate the third member along the longitudinal axis to move the balloon from a first length to a second length.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which:

FIG. 4 is a perspective view of a component of the device shown in FIG. 3;

FIG. 5 is a top view of a component of the device shown in FIG. 3;

FIG. 6 is a bottom view of a component of the device shown in FIG. 3;

FIG. 9 is a perspective view of a component of the device shown in FIG. 3;

FIG. 10 is a top view of a component of the device shown in FIG. 3;

FIG. 11 is a bottom view of a component of the device shown in FIG. 3;

FIG. 18 is a perspective view of a component of the device shown in FIG. 3;

FIG. 19 is a top view of a component of the device shown in FIG. 3;

FIG. 20 is a bottom view of a component of the device shown in FIG. 3;

FIG. 21A is a side view of a component of the device shown in FIG. 21;

FIG. 21B is an end view of the component shown in FIG. 21

FIG. 21C is an end view of the component shown in FIG. 21;

DETAILED DESCRIPTION

Figure 1:
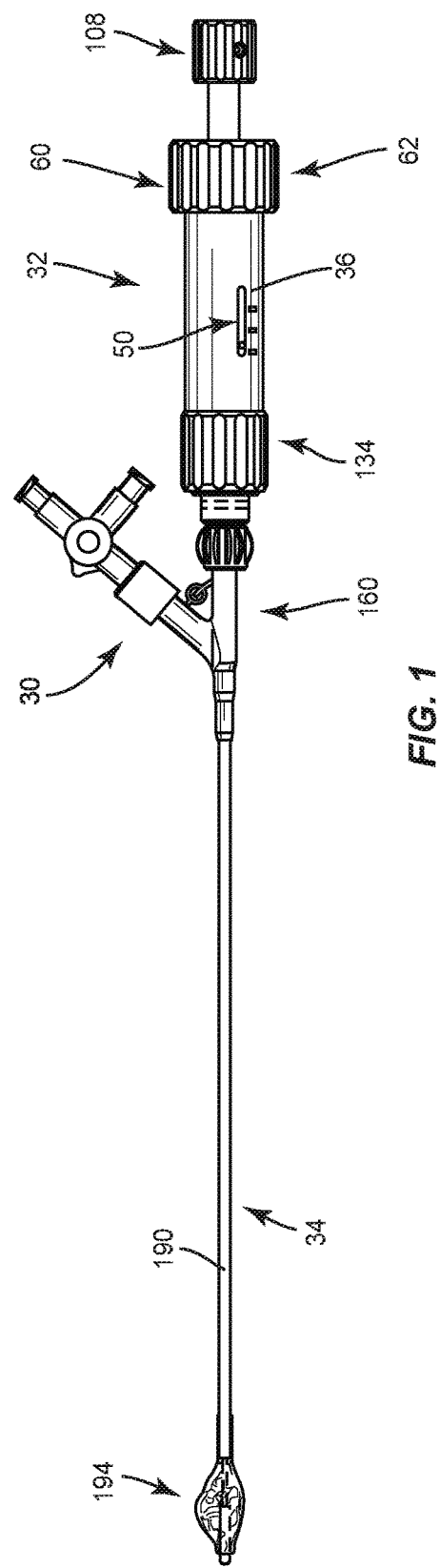
FIG. 1 is a side view of components of a surgical system in accordance with the principles of the present disclosure.
Figure 2:
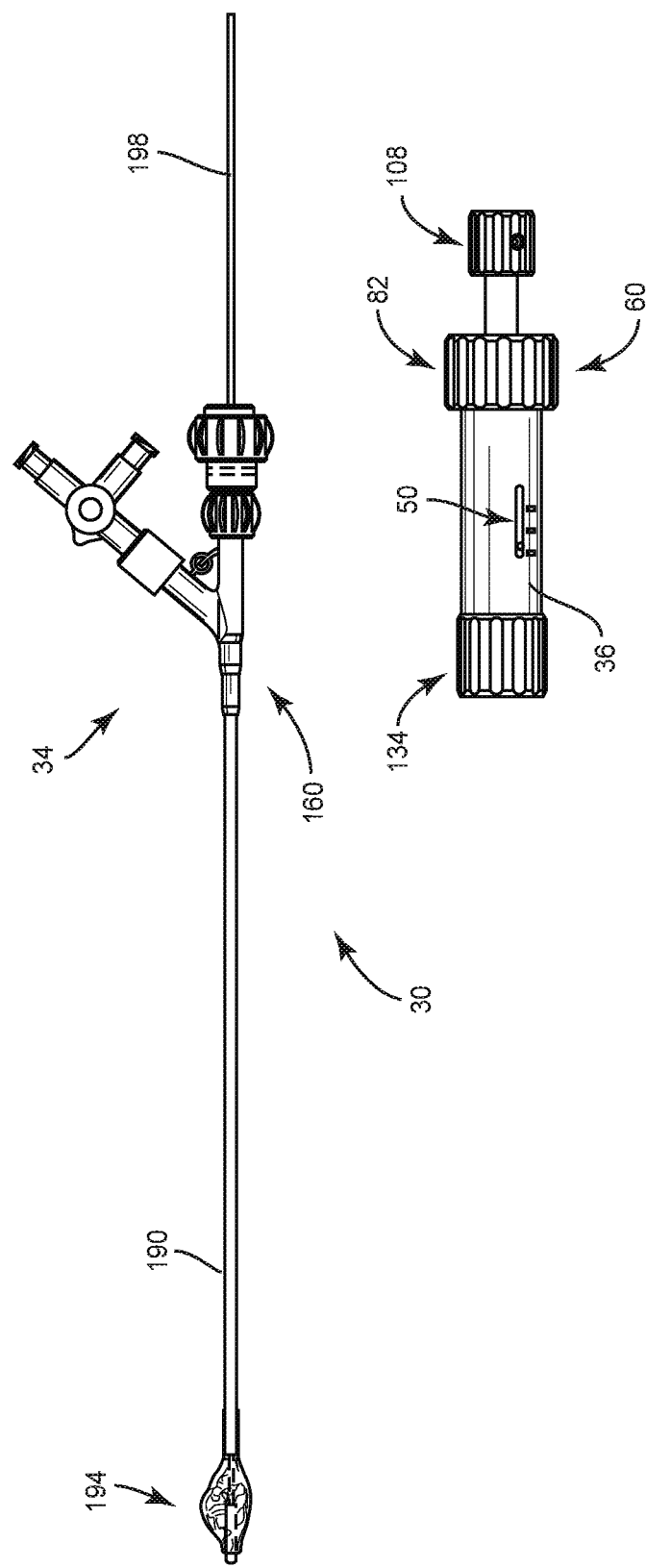
FIG. 2 is a side view of the system shown in FIG. 1, with devices separated.
Figure 3:
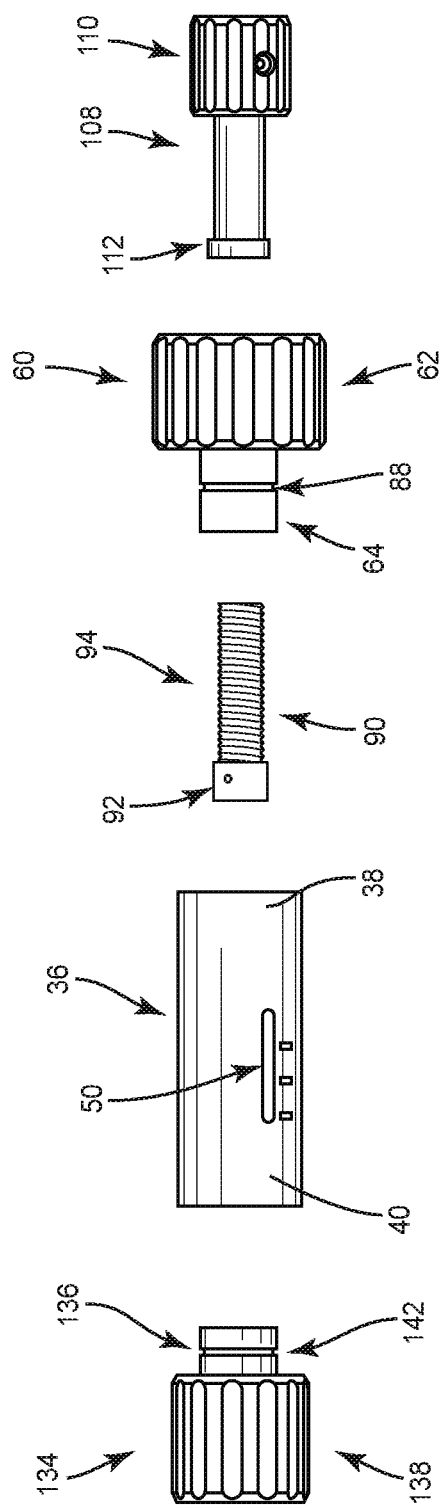
FIG. 3 is a side view of a device of the system shown in FIG. 1, with parts separated.

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding the numerical ranges and parameters set forth herein, the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" comprises any and all subranges between (and including) the minimum value of 1 and the maximum value of 10, that is, any and all subranges having a minimum value of equal to or greater than 1 and a maximum value of equal to or less than 10, e.g., 5.5 to 10.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be comprised within the invention as defined by the appended claims.

This disclosure is directed to a surgical system, such as, for example, a surgical system 30. In some embodiments, the components of surgical system 30 can be fabricated from biologically acceptable materials suitable for medical applications, including metals, synthetic polymers, ceramics and bone material and/or their composites, depending on the particular application and/or preference of a medical practitioner. For example, the components of surgical system 30, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyimide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 30 may have material composites, including the above materials, to achieve various desired characteristics such as strength, rigidity, elasticity, compliance, biomechanical performance, durability and radiolucency or imaging preference. The components of surgical system 30, individually or collectively, may also be fabricated from a heterogeneous material such as a combination of two or more of the above-described materials. The components of surgical system 30 may be monolithically formed, integrally connected or comprise fastening elements and/or instruments, as described herein.

Surgical system 30 comprises a device, such as, for example, an inflatable bone tamp withdrawal and longitudinal growth mechanism 32, and a device, such as, for example, an inflatable bone tamp 34. Mechanism 32 is configured to control the length of a balloon of inflatable bone tamp 34, as discussed herein. In particular, mechanism 32 is used to selectively decrease and/or increase the length of the balloon so that that the balloon will have a selected length upon expansion of the balloon. That is, the medical practitioner can use mechanism 32 to select a length of the balloon based upon the size of a cavity that is to be created in bone, for example, before the balloon is inserted into the patient and expanded. Mechanism 32 ensures that the balloon will have the selected length upon expansion and prevents underexpansion or overexpansion of the balloon.

Mechanism 32 comprises a main body, such as, for example, a body 36, shown in FIGS. 1-8, for example. Body 36 extends along a longitudinal axis L between an end 38 and an opposite end 40. Body 36 is a hollow cylinder that comprises an inner surface 42 that defines a cavity 44 that extends continuously from end 38 to end 40. Body 36 comprises an opening 44a that extends through an end surface of end 38 and an opening 44b that extends through an end surface of end 40. Openings 44a, 44b are in communication with cavity 44. Body 36 comprises a flange 46 in end 38, as shown in FIG. 5, and a flange 48 in end 40, as shown in FIG. 6. Flanges 46, 48 are connected to one another by inner surface 42. Flange 46 includes an aperture 46a (FIG. 5) that is in communication with cavity 44 and flange 48 includes an aperture 48a that is in communication with cavity 44.

In some embodiments, cavity 44 has a first diameter from flange 46 to flange 48 and a second diameter from flange 46 to an end surface of end 38 and from flange 48 to an end surface of end 40, the second diameter being greater than the first diameter. That is, cavity 44 has a reduced diameter between flanges 46, 48. In some embodiments, the reduced diameter of cavity 44 is equal to the diameters of apertures 46a, 46b. In some embodiments, cavity 44, opening 44a, opening 44b, aperture 46a and/or aperture 48a may have various cross section configurations, such as, for example, circular, oval, oblong, triangular, rectangular, square, polygonal, irregular, uniform, non-uniform, variable, tubular and/or tapered.

Figure 7:
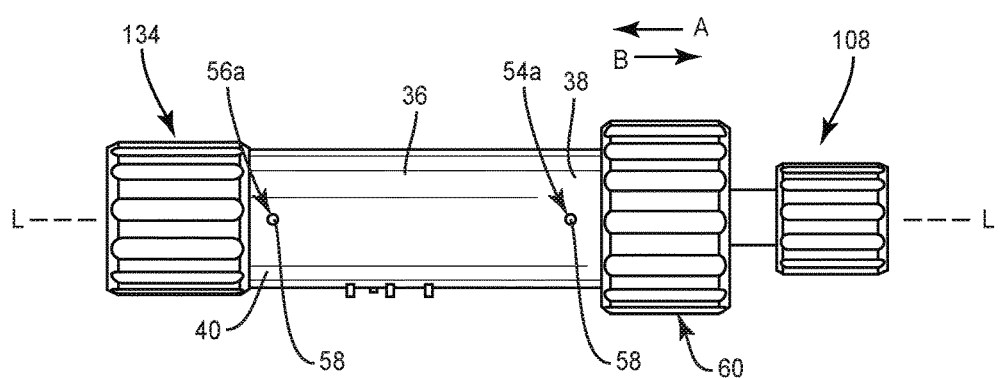
FIG. 7 is a side view of the device shown in FIG. 3.
Figure 8:
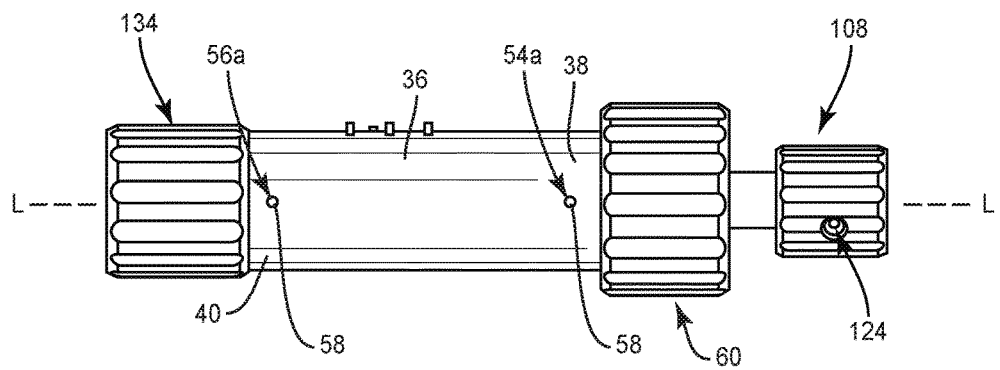
FIG. 8 is a side view of the device shown in FIG. 3.
Figure 12:
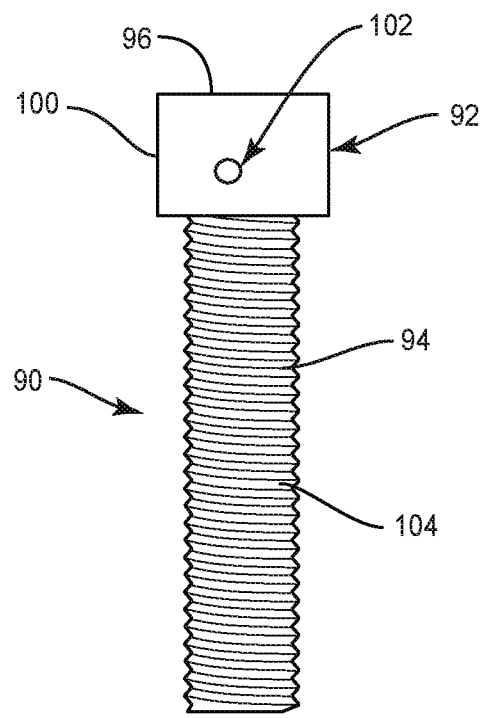
FIG. 12 is a side view of a component of the device shown in FIG. 3.
Figure 13:
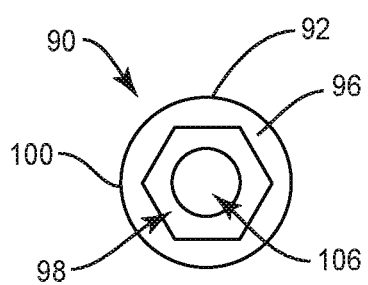
FIG. 13 is a top view of a component of the device shown in FIG. 3.

Body 36 includes a slot 50 that extends through inner surface 42 and an opposite outer surface 52 of body 36. Slot 50 is positioned between flanges 46, 48. Slot 50 has an elongated and/or oblong shape, as shown in FIGS. 1-4, 14A and 14B, for example. Slot 50 is configured for movably disposal of a pin, as discussed herein. Body 36 also includes a plurality of pin holes, such as for example, holes 54a, 54b in end 38 and holes 56a, 56b in a sidewall of end 40, as shown in FIGS. 4, 7 and 8. Holes 54a, 54b, 56a, 56b are each configured for fixed disposal of a pin, such as, for example, a pin 58, as discussed herein. Holes 54a, 54b are coaxial with one another and holes 56a, 56b are coaxial with one another. In some embodiments, holes 54a, 54b, 56a, 56b each extend perpendicular to longitudinal axis L. In some embodiments, slot 50, hole 54a, hole 54b, hole 56a and/or hole 56b may have various cross section configurations, such as, for example, circular, oval, oblong, triangular, rectangular, square, polygonal, irregular, uniform, non-uniform, variable, tubular and/or tapered.

A first member, such as, for example, a collar 60 (FIGS. 9-11) is positioned within a proximal end of cavity 44 such that collar 60 is rotatable relative to body 36 about longitudinal axis L. Collar 60 comprises a proximal end, such as, for example, a portion 62 and an opposite distal end, such as, for example, a portion 64. Portion 62 is fixed to collar 60. In some embodiments, portions 62, 64 are integrally formed and/or collar 60 is monolithic. Portion 62 has a diameter that is greater than a diameter of portion 64, as shown in FIGS. 9 and 11. In some embodiments, portion 64 has a diameter that is slightly less than that of cavity 44 between flange 46 and an end surface of end 38 of body 36 such that portion 64 can be inserted through opening 44a and into cavity 44, as discussed herein.

Portion 62 comprises a sidewall 66 having a plurality of spaced apart recesses, such as, for example, grooves 66a that are configured for gripping in order to rotate collar 60 relative to body 36 about longitudinal axis L. In some embodiments, grooves 66a each extend parallel to one another. In some embodiments, sidewall 66 extends parallel to longitudinal axis L. In some embodiments, grooves 66a each extend parallel to longitudinal axis L. Portion 62 comprises an end surface 68 that extends transverse to longitudinal axis L. In some embodiments, end surface 68 extends perpendicular to longitudinal axis L. In some embodiments, grooves 66a extend through end surface 68, as shown in FIG. 9, for example. In some embodiments, grooves 66a may be disposed at alternate orientations relative to longitudinal axis L, such as, for example, transverse, perpendicular and/or other angular orientations such as acute or obtuse, co-axial and/or may be offset or staggered.

Portion 62 includes one or a plurality of recesses 70 that extend through end surface 68. In some embodiments, portion 62 includes two recesses 70 that are spaced apart from one another, as shown in FIGS. 9 and 10. In some embodiments, recesses 70 each have an arcuate or arc configuration. In some embodiments, recesses 70 are blind holes that each extend through end surface 68 without extending through an opposite end surface 72 of portion 62. Sidewall 66 extends between and connects end surface 68 with end surface 72. In some embodiments, recesses 70 may be variously shaped, such as, for example, oval, oblong, triangular, square, polygonal, irregular, uniform, non-uniform, offset, staggered, undulating, arcuate, variable and/or tapered.

Portion 62 includes an inner surface 74 that defines a passageway 76. Passageway 76 is spaced apart from recesses 70. That is, passageway 76 is not in fluid communication with recesses 70. Inner surface 74 is smooth and free of threads or any other recesses or projections. A flange 78 extends outwardly from inner surface 74 and into passageway 76. Flange 78 includes an opening 80 that is in communication with passageway 76. Opening 80 has a diameter that is less than that of passageway 76, as shown in FIG. 10. Passageway 76 has a uniform diameter from flange 78 to end surface 68. In some embodiments, passageway 76 and/or opening 80 may have various cross section configurations, such as, for example, circular, oval, oblong, triangular, rectangular, square, polygonal, irregular, uniform, non-uniform, variable, tubular and/or tapered.

Portion 64 is cylindrical and includes a first threaded surface, such as, for example, a threaded inner surface 82 (FIG. 11) that defines a threaded bore 84 and an outer surface 86 opposite inner surface 82. In some embodiments, threaded inner surface 82 comprises a left-handed thread. Bore 84 is in communication with opening 80 and passageway 76 such that a second member, such as, for example, a bolt 90 can extend through bore 84 and opening 80 and into passageway 76, as discussed herein.

Portion 64 includes a circumferential groove 88 that extends into outer surface 86. Portion 64 is inserted through opening 44a of body 36 to position portion 64 within cavity 44 such that outer surface 86 of portion 64 engages inner surface 42 of body 36 in a manner that allows portion 64 to rotate within cavity 44. In some embodiments, an end surface of portion 64 that is opposite portion 62 engages flange 46 of body 36 when portion 64 is positioned within cavity 44 to prevent collar 60 from moving relative to body 36 along longitudinal axis L in direction A shown in FIG. 7. In some embodiments, end surface 72 of portion 62 engages the end surface of end 38 of body 36 when portion 64 is positioned within cavity 44 to prevent collar 60 from moving relative to body 36 along longitudinal axis L in direction A shown in FIG. 7. In some embodiments, pins 58 are inserted through holes 54a, 54b and into groove 88 to prevent portion 64 from moving relative to body 36 along longitudinal axis L in direction A or direction B shown in FIG. 7, while still allowing portion 64 to rotate relative to body 36 about longitudinal axis L.

Bolt 90 includes a head 92 and a shank 94 that extends from head 92. Shank 94 is fixed to head 92. Head 92 includes an end surface 96 that extends transverse to longitudinal axis L. A socket 98 extends into end surface 96. In some embodiments, socket 98 may have various cross section configurations, such as, for example, hexagonal, hexalobe, triangular, rectangular, square, polygonal, irregular, uniform, non-uniform, variable, tubular and/or tapered. Head 92 includes a side surface 100 that extends transverse to end surface 96. An aperture 102 extends into side surface 100 and is configured for disposal of one of pins 58, as discussed herein. Shank 94 includes a second threaded surface, such as, for example, a threaded outer surface 104 that engages threaded inner surface 82 of collar 60 to couple bolt 90 to collar 60. In some embodiments, threaded outer surface 104 comprises a left-handed thread configured to mate with threaded inner surface 82 to move bolt 90 relative to body 36 along longitudinal axis L upon rotation of collar 60, as discussed herein. Bolt 90 is cannulated. That is, an inner surface of bolt 90 defines a channel 106 configured for disposal of a portion of inflatable bone tamp 34, as discussed herein. Channel 106 extends through shank 94 and head 92 such that channel 106 is in communication with socket 98. Channel 106 has a diameter that is less than that of socket 98. In some embodiments, channel 106 has a uniform diameter. In some embodiments, bolt 90 does not include a socket, such as, for example, socket 98 and channel 106 extends through the entire length of bolt 90. That is, channel 106 extends through end surface 96 of head 92 and an opposite end surface of shank 94. In some embodiments, channel 106 may have various cross section configurations, such as, for example, circular, oval, oblong, triangular, rectangular, square, polygonal, irregular, uniform, non-uniform, variable, tubular and/or tapered.

Figure 14A:
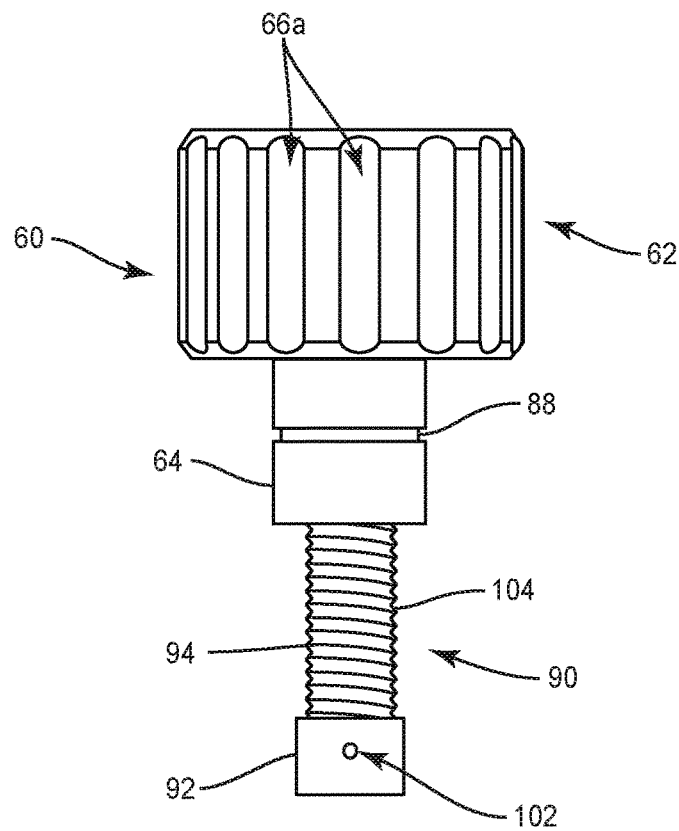
FIG. 14A is a side view of components of the device shown in FIG. 3.
Figure 14B:
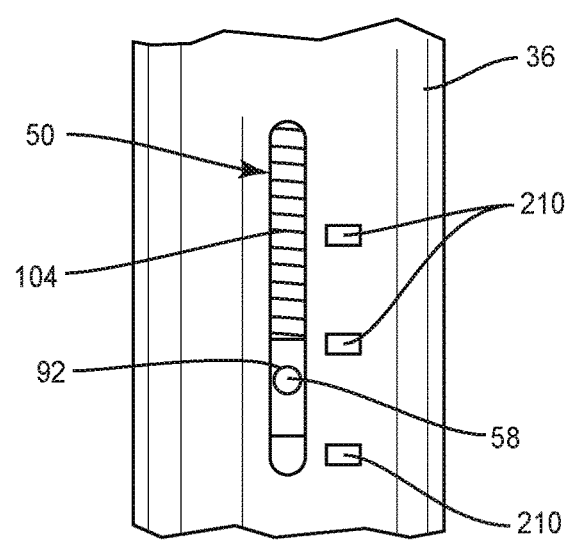
FIG. 14B is a side, close up view of a portion of the device shown in FIG. 3.
Figure 15:
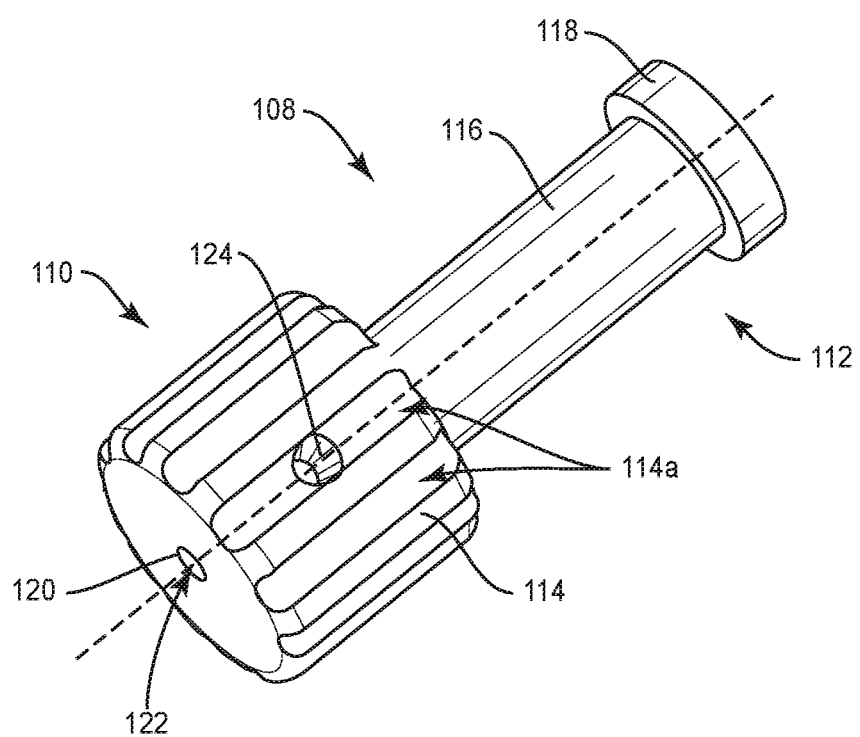
FIG. 15 is a perspective view of a component of the device shown in FIG. 3.
Figure 16:
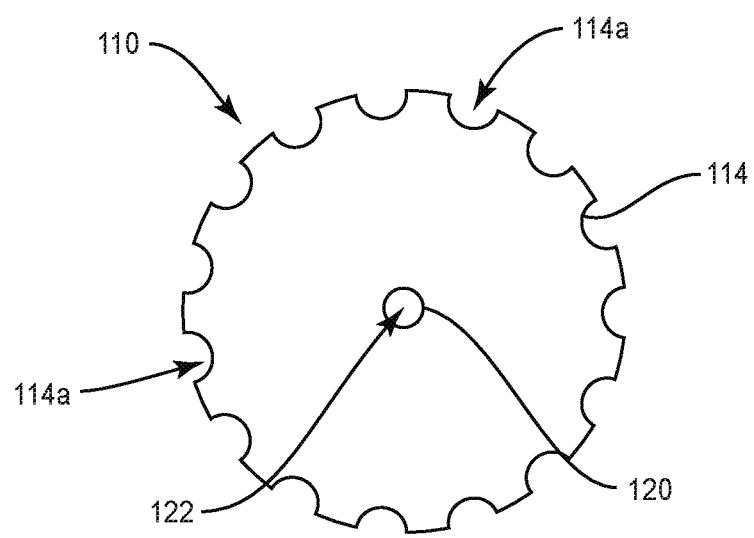
FIG. 16 is a top view of a component of the device shown in FIG. 3.

Threaded outer surface 104 of bolt 90 engages threaded inner surface 82 of collar 60 to couple bolt 90 to collar, as shown in FIG. 14A. Bolt 90 and portion 64 of collar 60 are then positioned within cavity 44 by inserting bolt 90 and portion 64 through opening 44a of body 36 leading with head 92 of bolt 90. Head 92 moves through opening 44a and aperture 46a of flange 46 such that head 92 is positioned between flanges 46, 48 and is visible through slot 50 in body 36, as shown in FIG. 14B. Head 92 has a diameter that is slightly less than the diameter of cavity 44 between flanges 46, 48 to prevent head 92 from wobbling within cavity 44 as head 92 moves along longitudinal axis L within cavity 44.

One of pins 58 is positioned through slot 50 and into aperture 102 in head 92 such that pin 58 is fixed to head 92. Pin 58 extends through slot 50 when pin 58 is positioned within aperture 102 to prevent rotation of bolt 90 relative to body 36 about longitudinal axis L. Collar 60 is prevented from moving relative to body 36 along longitudinal axis L due to pins 58 in holes 46a, 46b that extend into groove 50, and bolt 90 is prevented from rotating relative to body 36 due to pin 58 in head 92 that extends through slot 50. Bolt 90 translates relative to body 36 and collar 60 along longitudinal axis L in a first direction, such as, for example, direction A shown in FIG. 7. Collar 60 is rotated relative to body 36 in a first rotational direction, such as, for example, counterclockwise, and translates relative to body 36 and collar 60 along longitudinal axis L in a second direction, such as, for example, direction B shown in FIG. 7. Collar 60 is then rotated relative to body 36 in a second rotational direction, such as, for example, clockwise, as discussed herein. This allows shank 94 to be selectively moved relative to collar 60 such that a tip or end surface of shank 94 may be positioned within threaded bore 84 or may be moved up and down within passageway 76. That is, once the tip of shank 94 exits threaded bore 84, the tip of shank 94 may be selectively moved up and down within passageway 76 by rotating collar 60 relative to body 36 in the first rotational direction or the second rotational direction. It is envisioned that threaded outer surface 104 and threaded inner surface 82 may both include right-handed threads. Collar 60 would then translate along longitudinal axis L in direction B when collar 60 is rotated counterclockwise relative to body 36, and would translate along longitudinal axis L in direction A when collar 60 is rotated clockwise relative to body 36.

A third member, such as, for example stylet knob 108 extends from a proximal end 110 to a distal end 112. End 112 is fixed relative to end 110. In some embodiments, end 110 is integrally formed with end 112 and/or knob 108 is monolithic. End 112 is configured to be positioned within passageway 76 of collar 60. End 110 comprises a sidewall 114 having a plurality of spaced apart recesses, such as, for example, grooves 114a that are configured for gripping in order to rotate knob 108 relative to body 36 and collar 60. In some embodiments, grooves 114a each extend parallel to one another. In some embodiments, sidewall 114 extends parallel to longitudinal axis L. In some embodiments, grooves 114a each extend parallel to longitudinal axis L. End 112 includes a cylindrical shaft 116 having a uniform diameter and an enlarged portion 118 having a diameter that is greater than the diameter of shaft 116. The diameter of portion 118 is slightly less than the diameter of passageway 76 to prevent knob 108 from wobbling as knob 108 moves along longitudinal axis L within passageway 76.

Knob 108 includes an inner surface 120 that defines a lumen 122 configured for disposal of a component of inflatable bone tamp 34, a discussed herein. Lumen 122 extends through an end surface of end 110 and an opposite end surface of portion 118. Lumen 122 has a diameter that is less than that of shank 94 of bolt 90 to prevent bolt 90 from being inserted into lumen 122. In some embodiments, lumen 122 extends through the end surface of portion 118 without extending through the end surface of end 110. In some embodiments, knob 108 includes an aperture 124 that extends through sidewall 114. Aperture 124 is in communication with lumen 122 and is configured for disposal of a fastener, such as, for example, a set screw, such that the set screw engages a component of inflatable bone tamp 34 within lumen 122 to fix the component relative to knob 108, as discussed herein.

Figure 17:
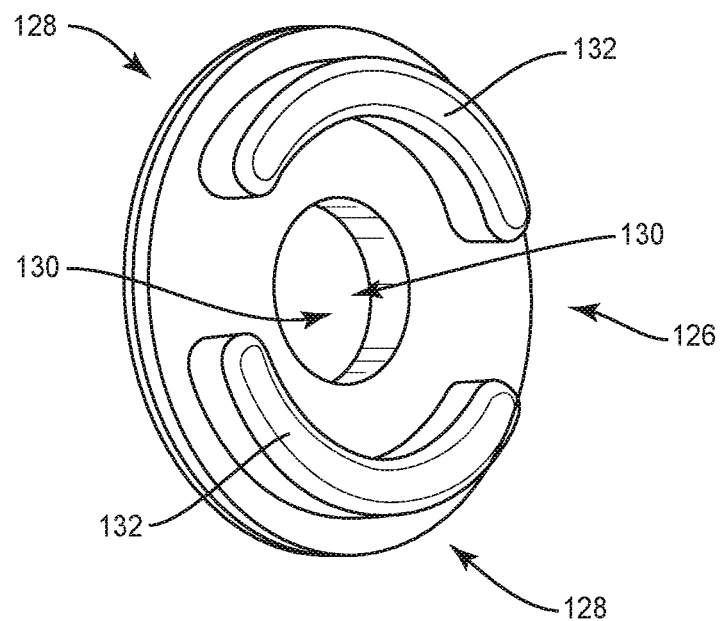
FIG. 17 is a perspective view of a component of the device shown in FIG. 3.

In some embodiments, a cap 126 shown in FIG. 17 is used to maintain end 110 of knob 108 within passageway 76 of collar 60. In some embodiments, cap 126 is made up of separate halves 128 that each include a cutout 130 and a projection 132. Projections 132 each have an arcuate configuration and are configured for disposal in one of recesses 70 in collar 60. When halves 128 are positioned within recesses 70, cutouts 130 define an opening that is aligned with passageway 76. That is, the opening defined by cutouts 130 is coaxial with passageway 76 to allow shaft 116 of knob 108 to extend through the opening defined by cutouts 130 when portion 118 of knob 108 is positioned within passageway 76. The opening defined by cutouts 130 is slightly larger than the diameter of shaft 116 to prevent knob 108 from wobbling as knob 108 moves relative to body 36 and collar 60 along longitudinal axis L. In some embodiments, the diameter of portion 118 is larger than the diameter of the opening defined by cutouts 130 to prevent portion 118 from being removed from passageway 76 of collar 60 through the opening defined by cutouts 130. It is envisioned that cap 126 may include features in place of, or in addition to projections 132 to couple cap 126 to collar 60. For example, in some embodiments, cap 126 can be variously connected with collar 60, such as, for example, monolithic, integral connection, frictional engagement, threaded engagement, mutual grooves, screws, adhesive, nails, barbs and/or raised element.

In some embodiments, cap 126 is one piece. That is, cap 126 is monolithically formed. In some embodiments, cap 126 is made from a flexible and/or resilient material such that the opening in cap 126 can expand as cap 126 is moved over portion 118 of knob 108 and then contracts when the opening in cap 126 is positioned about shaft 116 of knob 108. In some embodiments, cap 126 may be made from a rigid material. In some embodiments, knob 108 may be made from two pieces. For example, portion 118 of knob 108 may be removable from shaft 116 of knob 108. As such, cap 126 can be positioned over shaft 116 such that the opening in cap 126 is positioned about shaft 116. Portion 118 may then be coupled to shaft 116. In some embodiments, shaft 116 comprises threads that engage threads of portion 118 to couple portion 118 to shaft 116.

In some embodiments, mechanism 32 includes a fourth member, such as, for example, a second collar 134 shown in FIGS. 18-20. Collar 134 includes a proximal end 136 and a distal end 138. End 136 is configured to be positioned within a distal end of cavity 44 such that collar 134 is rotatable relative to body 36. End 136 is fixed to end 138. In some embodiments, ends 136, 138 are integrally formed and/or collar 134 is monolithic. End 138 has a diameter that is greater than a diameter of end 136, as shown in FIGS. 18 and 19. In some embodiments, end 136 has a diameter that is slightly less than that of cavity 44 between flange 48 and an end surface of end 40 of body 36 such that end 136 can be inserted through opening 44b and into cavity 44, as discussed herein.

End 136 is cylindrical and includes an outer surface 140 and a circumferential groove 142 that extends into outer surface 140. End 136 is inserted through opening 44b of body 36 to position end 136 within cavity 44 such that outer surface 140 of end 136 engages inner surface 42 of body 36 in a manner that allows end 136 to rotate within cavity 44 about longitudinal axis L. In some embodiments, an end surface of end 136 that is opposite end 138 engages flange 48 of body 36 when end 136 is positioned within cavity 44 to prevent collar 134 from moving relative to body 36 along longitudinal axis L in direction B shown in FIG. 7. In some embodiments, pins 58 are inserted through holes 56a, 56b and into groove 142 to prevent end 136 from moving relative to body 36 along longitudinal axis L in direction A or direction B shown in FIG. 7, while still allowing end 136 to rotate relative to body 36 about longitudinal axis L.

End 138 comprises a sidewall 144 having a plurality of spaced apart recesses, such as, for example, grooves 144a that are configured for gripping in order to rotate collar 134 relative to body 36. In some embodiments, grooves 144a each extend parallel to one another. In some embodiments, sidewall 144 extends parallel to longitudinal axis L. In some embodiments, grooves 144a each extend parallel to longitudinal axis L. End 138 comprises an end surface 146 and an opposite end surface 148. End surfaces 146, 148 each extend transverse to longitudinal axis L. In some embodiments, end surfaces 146, 148 each extend perpendicular to longitudinal axis L. In some embodiments, end surface 146 engages the end surface of end 40 of body 36 when end 136 is positioned within cavity 44 to prevent collar 134 from moving relative to body 36 along longitudinal axis L in direction B shown in FIG. 7. In some embodiments, grooves 144a extend through end surfaces 146, 148. Sidewall 144 extends between and connects end surface 146 with end surface 148. In some embodiments, grooves 144a may be disposed at alternate orientations, relative to longitudinal axis L, such as, for example, transverse, perpendicular and/or other angular orientations such as acute or obtuse, co-axial and/or may be offset or staggered. Sidewall 144 includes an inner surface 150 that defines a socket 152, as shown in FIGS. 18 and 20. Inner surface 150 includes a plurality of indents 154 that are spaced apart from one another by gaps 156. End 136 includes an opening 158 that is in communication with socket 152 such that a component of inflatable bone tamp 34 can extend through opening 158 when an adapter 160 is positioned within socket 152, as discussed herein.

Figure 21:
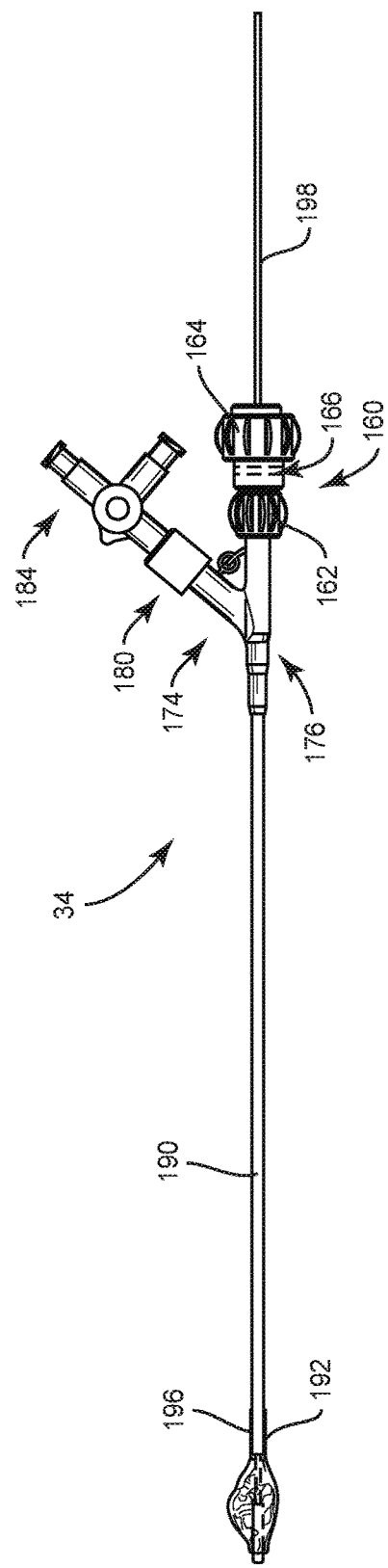
FIG. 21 is a side view of a device of the system shown in FIG. 1.
Figure 22A:
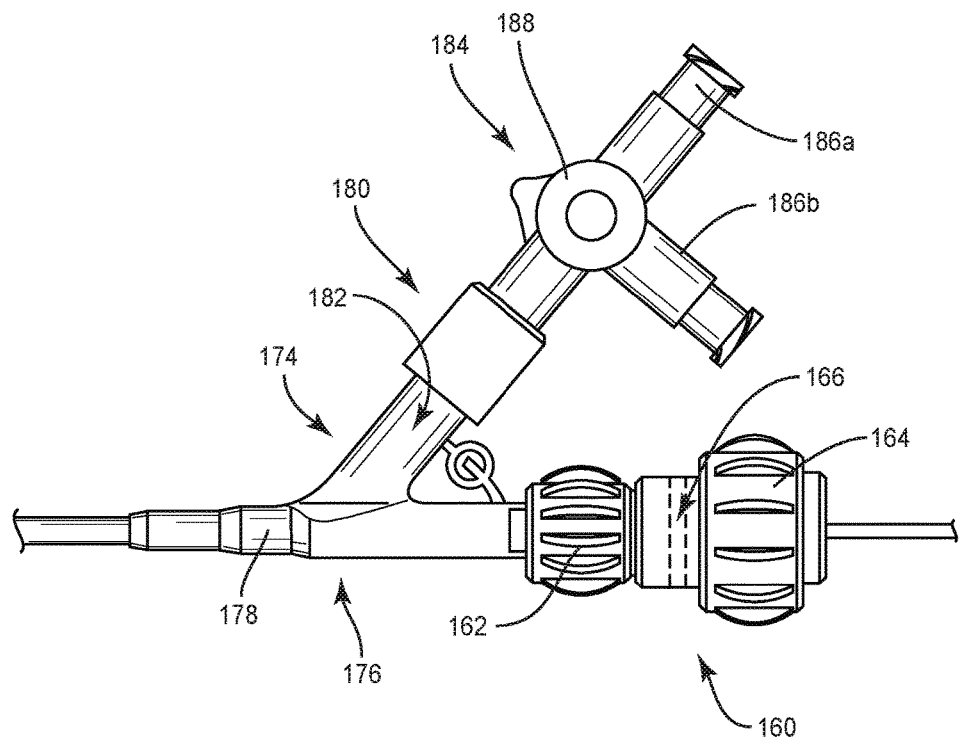
FIG. 22A is a side, close up view of a portion of the device shown in FIG. 21.

Adapter 160 is shown in FIGS. 21-22A, for example. In some embodiments, adapter 160 is a Tuohy borst. Adapter 160 includes a body 162 and a fitting 164 that is rotatable relative to body 162. Body 162 includes a valve 166 positioned within body 162. Valve 166 opens and closes upon rotation of fitting 164 relative to body 162 about longitudinal axis L. In some embodiments, threads of fitting 164 engage threads of body 162 such that rotating fitting 164 relative to body 162 in a first rotational direction, such as, for example, clockwise, causes fitting 164 to translate relative to body 162 in direction C shown in FIG. 21A. Rotating fitting 164 relative to body 162 in a second rotational direction, such as, for example, counterclockwise, causes fitting 164 to translate relative to body 162 in direction D shown in FIG. 21A. Moving fitting 164 relative to body 162 in direction C causes valve 166 to move from a vented or open position shown in FIG. 21B to a sealed or closed position shown in FIG. 21C. In some embodiments, moving fitting 164 in direction C causes a washer or gasket of fitting 164 to push valve 166 such that valve 166 engages a surface, such as, for example, a tapered surface of body 162 to move valve 166 from the open position to the closed position. In some embodiments, valve 166 is biased to the open position such that moving fitting 164 in direction D causes a washer or gasket of fitting 164 to become spaced apart from valve 166 to move valve 166 from the closed position to the open position.

Fitting 164 is configured for disposal in socket 152 of collar 134 to fix fitting 164 relative to collar 134 such that rotating collar 134 about longitudinal axis L also rotates collar 134 about longitudinal axis L. Fitting 164 includes a plurality of spaced apart ridges 168 that extend from an outer surface 170 of fitting 164. When fitting 164 is positioned within socket 152, outer surface 170 of fitting 164 engages indents 154 such that ridges 168 are disposed in gaps 156 in socket 152 to prevent rotation of fitting 164 relative to collar 134. Body 162 includes a channel 172 that is aligned with opening 158 of collar 134 when fitting 164 is positioned within socket 152 such that a component of inflatable bone tamp 34 can be inserted through channel 172 and opening 158 when valve 166 is in the open position. Moving valve 166 from the open position to the closed position will then fix the component relative to mechanism 32 and/or inflatable bone tamp 34, as discussed herein.

A connector 174 is coupled to adapter 160. Connector 174 includes a stem 176 having a passage 178 that extends therethrough, as shown in FIG. 22A. Stem 176 is coupled to body 162 of adapter 160 such that passage 178 is in communication with channel 172. In some embodiments, passage 178 is coaxial with channel 172. In some embodiments, stem 176 is positioned within body 162 and is fixed to body 162 using an adhesive or other bonding material, for example to prevent stem 176 from moving relative to body 162. Connector 174 includes a port 180 connected to stem 176. Port 180 includes a lumen 182 (FIG. 22A) that is in communication with passage 178 such that a material, such as, for example, an inflation material can be injected through lumen 182 and into passage 178. In some embodiments, connector 174 includes a coupling 184 that is attached to port 180. Coupling 184 includes a first conduit 186a, a second conduit 186b and a valve 188. Valve 188 is rotatable relative to port 180 between a first configuration in which conduit 186a is in communication with lumen 182 and conduit 186b is closed off from lumen 182 by valve 188, and a second configuration in which conduit 186b is in communication with lumen 182 and conduit 186a is closed off from lumen 182 by valve 188.

Figure 22B:
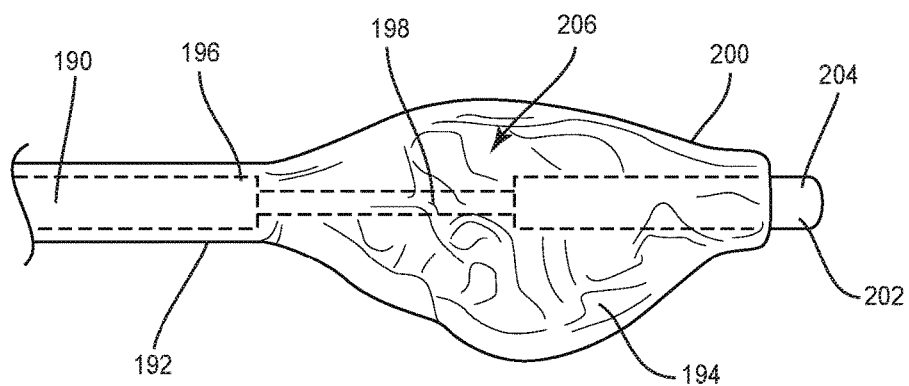
FIG. 22B is a side, close up view of a portion of the device shown in FIG. 21.

An outer shaft 190 of inflatable bone tamp 34 is coupled to connector 174 such that outer shaft 190 is fixed to connector 174. Outer shaft 190 is a hollow tube. In some embodiments, outer shaft 190 is coupled to connector 174 using an adhesive or other bonding material. In some embodiments, outer shaft 190 is rigid such that outer shaft 190 cannot be bent without breaking to provide strength to outer shaft 190. In some embodiments, outer shaft 190 is flexible such that outer shaft 190 can be bent without breaking to allow outer shaft 190 to be bent as outer shaft 190 is guided through a patient's anatomy. In some embodiments, outer shaft 190 comprises a radiopaque material. A proximal end 192 of an expandable member, such as, for example, a balloon 194 is coupled to a distal end 196 of outer shaft 190, as shown in FIG. 22B, for example. A stylet, such as, for example, an inner shaft 198 extends through outer shaft 190 such that a distal end 200 of balloon 194 is coupled to a distal end 202 of inner shaft 198. In some embodiments, distal end 202 of inner shaft 198 extends beyond distal end 200 of balloon 194, as shown in FIG. 22B. In some embodiments, inner shaft 198 has a uniform diameter from proximal end 192 to a tip 204 at distal end 202 of inner shaft 198. Tip 204 has a diameter that is greater than the hollow portion of outer shaft 190 to prevent tip 204 from being inserted into outer shaft 190. In some embodiments, tip 204 has a diameter that is equal to or greater than the diameter of outer shaft 190. A portion of tip 204 is positioned within a fillable cavity 206 of balloon 194.

Figure 23:
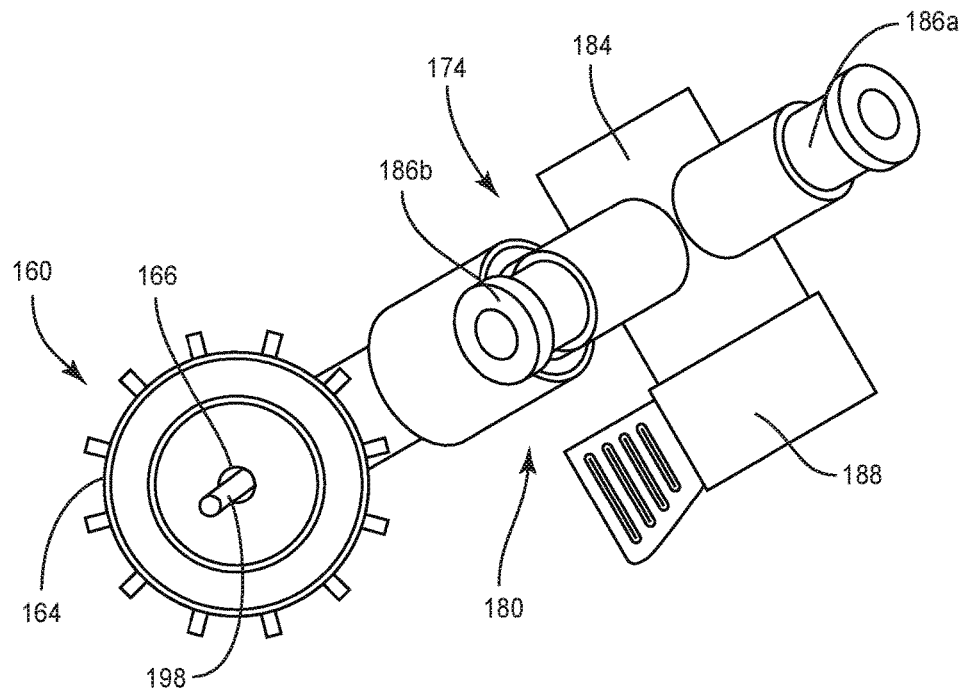
FIG. 23 is a top view of the device shown in FIG. 21.
Figure 24:
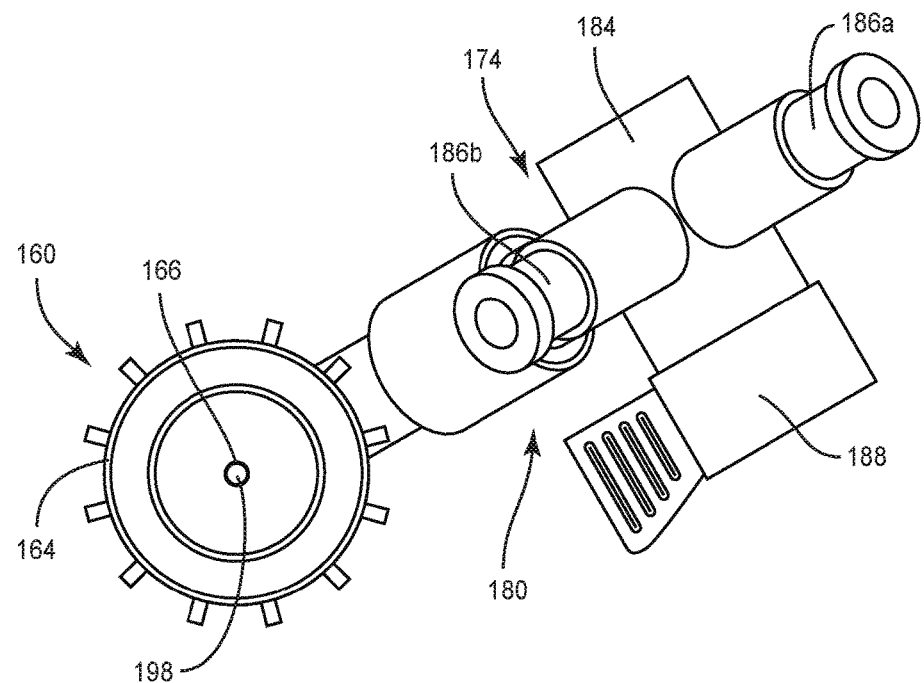
FIG. 24 is a top view of the device shown in FIG. 21.

Inner shaft 198 extends through outer shaft 190, lumen 182 of port 180, channel 172 of adapter 160, opening 158 of collar 134, channel 106 of bolt 90, passageway 76 of collar 60 and lumen 122 of knob 108. In some embodiments, inner shaft 198 is movable between a first configuration in which inner shaft 198 is able to translate along longitudinal axis L to a second configuration in which inner shaft 198 is fixed relative to mechanism 32, adapter 160, connector 174 and outer shaft 190. Inner shaft 198 is moved from the first configuration to the second configuration by rotating fitting 164 of adapter 160 relative to body 162 of adapter 160 in the first rotational direction or the second rotational direction to cause fitting 164 to move relative to body 162 in direction C to move valve 166 from the vented or open position shown in FIGS. 21B and 23 to the sealed or closed position shown in FIGS. 21C and 24. When valve 166 is in the closed position, valve 166 engages inner shaft 198, as shown in FIG. 24, to prevent inner shaft 198 from moving relative to mechanism 32, adapter 160, connector 174 and outer shaft 190 along longitudinal axis L. In some embodiments, a set screw is positioned in aperture 124 of knob 108 when inner shaft 198 is positioned within lumen 122 to fix inner shaft 198 relative to knob 108. This allows balloon 194 to move along longitudinal axis L in direction A or direction B when knob 108 moves in direction A or direction B and to rotate about longitudinal axis L when knob 108 is rotated about longitudinal axis L, as discussed herein.

In some embodiments, system 30 is assembled by engaging threaded outer surface 104 of bolt 90 with threaded inner surface 82 of collar 60 to couple bolt 90 to collar 60, as shown in FIG. 14A. Collar 60 and bolt 90 are inserted through opening 44a of body 36 and into cavity 44 of body 36 until the end surface of portion 64 of collar 60 engages flange 46 of body 36 to prevent collar 60 from moving relative to body 36 along longitudinal axis L in direction A shown in FIG. 7. Head 92 of bolt 90 is positioned in cavity 44 of body 36 between flanges 46, 48 of body 36, as discussed herein. One of pins 58 is positioned through slot 50 of body 36 and into aperture 102 in head 92 of bolt 90 such that pin 58 is fixed to head 92. Pin 58 extends through slot 50 when pin 58 is positioned within aperture 102 to prevent rotation of bolt 90 relative to body 36 about longitudinal axis L. Pins 58 are inserted through holes 54a, 54b in body 36 and into groove 88 of collar 60 to prevent collar 60 from moving relative to body 36 along longitudinal axis L in direction A or direction B shown in FIG. 7, while still allowing collar 60 to rotate relative to body 36 about longitudinal axis L.

Knob 108 is inserted into passageway 76 of collar 60 until portion 118 of knob 108 engages flange 78 of collar 60. Projections 132 of cap 126 are positioned in recesses 70 in collar 60 such that shaft 116 of knob 108 extends through the opening defined by cutouts 130 of cap 126. In some embodiments, an adhesive or other bonding material is placed within recesses 70 before projections 132 are inserted into recesses 70 to bond cap 126 to collar 134.

Collar 134 is inserted into cavity 44 of body 36 by moving end 136 of collar 134 through opening 44b of body 36 to position end 136 within cavity 44 such that outer surface 140 of end 136 engages inner surface 42 of body 36 and the end surface of end 136 engages flange 48 of body 36 to prevent collar 134 from moving relative to body 36 along longitudinal axis L in direction B shown in FIG. 7. Pins 58 are inserted through holes 56a, 56b and into groove 142 to prevent end 136 from moving relative to body 36 along longitudinal axis L in direction A or direction B shown in FIG. 7, while still allowing end 136 to rotate relative to body 36 about longitudinal axis L.

Inner shaft 198 is moved through outer shaft 190, lumen 182 of port 180, channel 172 of adapter 160, opening 158 of collar 134, channel 106 of bolt 90, passageway 76 of collar 60 and lumen 122 of knob 108. Set screw 208 is positioned in aperture 124 of knob 108 when inner shaft 198 is positioned within lumen 122 to fix inner shaft 198 relative to knob 108, as discussed herein. Fitting 164 of adapter 160 is positioned within socket 152 of collar 134 such that outer surface 170 of fitting 164 engages indents 154 and ridges 168 are disposed in gaps 156 in socket 152 to prevent rotation of fitting 164 relative to collar 134 about longitudinal axis L.

In operation and use, to treat a bone disorder, such as, for example, a spinal fracture, a medical practitioner obtains access to a target location including at least one vertebra, such as, for example, a fractured vertebra, in any appropriate manner, such as through incision and retraction of tissue. It is envisioned that the system 30 may be used in any existing surgical method or technique including open surgery, mini-open surgery, minimally invasive surgery including percutaneous surgical implantation, whereby vertebra V is accessed through a micro-incision, or sleeve that provides a protected passageway to the area. Once access to the surgical site(s) are obtained, the particular surgical procedure is performed for treating the bone disorder.

Inflatable bone tamp 34 is moved through the incision and positioned so that balloon 194 is positioned within a vertebral body of the fractured vertebra. Mechanism 32, adapter 160 and connecter 174 are positioned outside of the patient when balloon 194 is positioned within the vertebral body to allow the medical practitioner to manipulate mechanism 32, adapter 160 and connecter 174, as discussed herein. In some embodiments, balloon 194 is moved into the vertebral body when balloon 194 is in an uninflated configuration shown in FIG. 25B. Balloon 194 is movable from the uninflated configuration to an inflated configuration (FIG. 25C) by injecting an inflation material, such as, for example, air, saline, or a contrast solution through one of conduits 186a, 186b such that the inflation material moves through lumen 182 of port 180 and outer shaft 190 and into cavity 206 of balloon 194. In some embodiments, balloon 194 is moved from the uninflated configuration to the inflated configuration by moving the inflation material through conduit 186a when valve 188 is in the first configuration discussed above. In some embodiments, balloon 194 is moved from the uninflated configuration to the inflated configuration by moving the inflation material through conduit 186b when valve 188 is in the second configuration discussed above. In some embodiments, valve 166 is moved from the vented or open position shown in FIG. 21B to the sealed or closed position shown in FIG. 21C to prevent the inflation material from escaping in order to maintain balloon 194 in the inflated configuration.

As balloon 194 moves from the uninflated configuration to the inflated configuration, balloon 194 creates a cavity within the vertebral body. Mechanism 32 may be manipulated to control the size of the cavity created by balloon 194. For example, mechanism can be used to allow a medical practitioner to select the length of balloon 194 when balloon 194 is in the inflated configuration by rotating collar 60 relative to body 36 about longitudinal axis L to increase the length of balloon 194 from a first length shown in FIG. 25A to a second length shown in FIG. 25B.

When balloon 194 has the first length, a proximal tip of bolt 90 is positioned within passageway 76 of collar 60 and portion 118 of knob 108 engages cap 126. Rotating collar 60 relative to body 36 in a first rotational direction, such as, for example, clockwise, causes bolt 90 to translate relative to collar 60 and body 36 in direction A such that bolt 90 moves in direction A within passageway 76. This causes knob 108 to move relative to collar 60 in direction A within passageway 76 of collar 60. Knob 108 moves in direction A, the distal tip of inner shaft 198 moves away from outer shaft 190 to increase the length of balloon 194 from the first length shown in FIG. 25A to the second length shown in FIG. 25B. In some embodiments, the proximal tip of bolt 90 is positioned within threaded bore 84 of collar 60 and portion 118 of knob 108 engages flange 76 when balloon 194 has the second length. As would be apparent to one of ordinary skill in the art, mechanism 32 may be used to manipulate balloon 194 such that balloon 194 has any length that is greater than the first length and less than the second length by rotating collar 60 relative to body 36 in the manner discussed above. In some embodiments, balloon 194 is moved from the uninflated configuration to the inflated configuration when balloon 194 has a length greater than the first length, such as, for example, the second length, as shown in FIG. 25C.

Figure 25A:
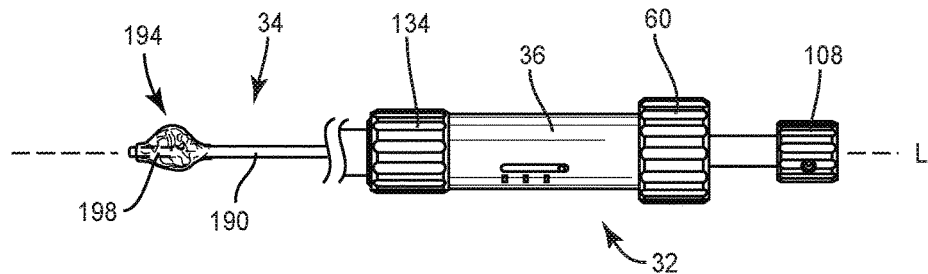
FIG. 25A is a side view of the system shown in FIG. 1.
Figure 25B:
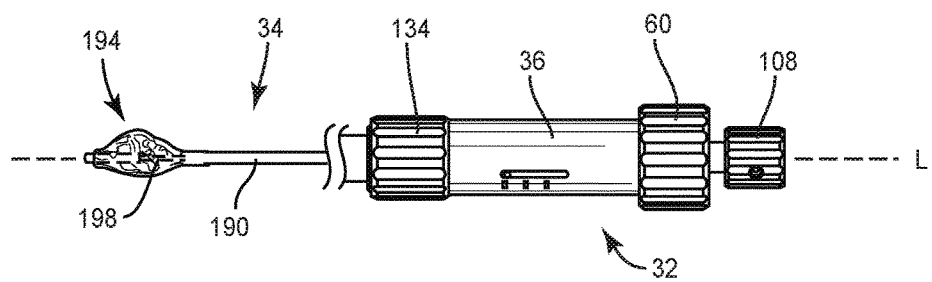
FIG. 25B is a side view of the system shown in FIG. 1.
Figure 25C:
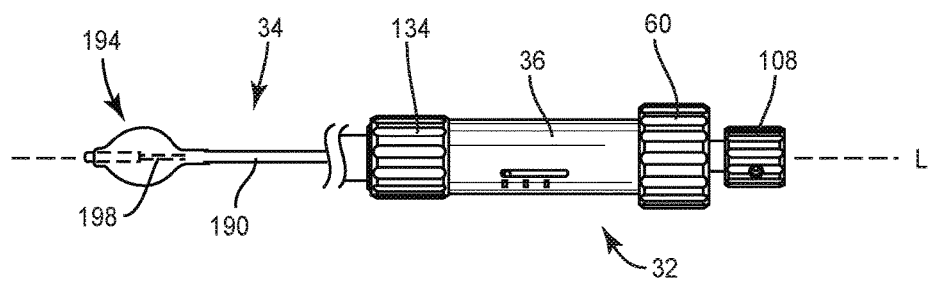
FIG. 25C is a side view of the system shown in FIG. 1.

As mechanism 32 is manipulated to move balloon 194 from the first length to the second length, pin 58 that is positioned within aperture 102 of bolt 90 moves from a proximal end of slot 50 to a distal end of slot 50, as shown in FIGS. 25A and 25B. In some embodiments, body 36 includes graduation markings 210 along slot 50 to indicate the length of balloon 194. The position of pin 58 that extends through slot 50 can thus be used to determine the length of balloon 194 by comparing the position of pin 58 to graduation markings 210. This allows a medical practitioner to visually confirm the length of balloon 194 when balloon 194 is positioned within a patient, thus eliminating the need to remove balloon 194 from the patient to determine the length of balloon 194.

Figure 25D:
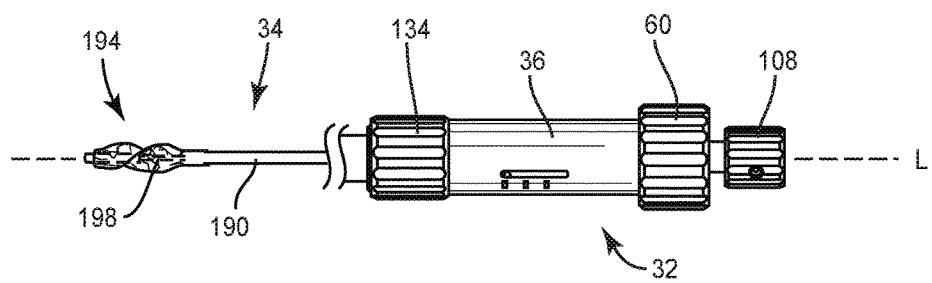
FIG. 25D is a side view of the system shown in FIG. 1.

In some embodiments, balloon 194 is moved from the inflated configuration to the uninflated configuration before removing balloon 194 from the patient in order to prevent and/or reduce the likelihood of injury or trauma to the patient. In some embodiments, valve 166 is moved from the sealed or closed position shown in FIG. 21C to the vented or open position shown in FIG. 21B to allow the inflation material to escape, thus causing balloon 194 to move from the inflated configuration to the uninflated configuration. Knob 108 is rotated relative to collar 60 and/or body 36 in the first rotational direction or the second rotational direction thus causing balloon 194 to twist about inner shaft 198, as shown in FIG. 25D to reduce the profile of balloon 194. Balloon 194 is then removed from the patient. In some embodiments, the cavity created by balloon 194 is filled with a material, such as, for example, bone cement.

In some embodiments, balloon 194 is configured such that balloon 194 is twisted about inner shaft 198 without rotating knob 108 relative to collar 60. This allows inflatable bone tamp 34 to be delivered with balloon 194 twisted about inner shaft 198 without applying any external force, such as, for example, rotating knob 108 relative to collar 60. In such embodiments, balloon 194 can be moved through the incision and positioned so that balloon 194 is positioned within a vertebral body of the fractured vertebra while balloon 194 is twisted about inner shaft 109. This allows balloon 194 to be inserted into the patient while balloon 194 has a first profile. As balloon 194 is moved from the uninflated configuration to the inflated configuration, knob 108 rotates relative to collar 60 to move balloon 194 from a first configuration in which balloon 194 is twisted about and has the first profile to a second configuration in which balloon 194 is untwisted and has a second profile that is greater than the first profile. Moving balloon 194 from the inflated configuration to the uninflated configuration causes knob 108 to rotate relative to collar 60, which moves balloon 194 from the second configuration to the first configuration. Balloon 194 can then be removed from the patient with balloon 194 in the first configuration with the reduced first profile to minimize injury or trauma to the patient as balloon 194 is removed from the patient. In some embodiments, balloon 194 comprises a material having a memory to allow balloon 194 to be twisted about inner shaft 198 without applying any external force to balloon 194 (e.g., rotation of knob 108 relative to collar 60) such that balloon 194 will return to the twisted configuration if no external forces are applied to balloon 194.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:
1. A surgical system comprising:
a body extending along a longitudinal axis;
a first member rotatably positioned within the body and comprising a first threaded surface;
a second member positioned within the body and comprising a second threaded surface that engages the first threaded surface, the second member being non-rotatable relative to the body;
a third member positioned within the first member; and
an inflatable bone tamp comprising:
an outer shaft coupled to the body,
a balloon coupled to the outer shaft, and an inner shaft coupled to the third member and the balloon, wherein the first member is rotatable relative to the body to translate the third member along the longitudinal axis to move the balloon from a first length to a second length.

2. A system as recited in claim 1, wherein the inner shaft extends through the first and second members, a proximal end of the inner shaft being fixed to the third member and a distal end of the inner shaft being fixed to the balloon.

3. A system as recited in claim 1, wherein the third member comprises a lumen, the inner shaft being positioned within the lumen.

4. A system as recited in claim 1, wherein the body comprises an inner surface defining a cavity and a flange, a distal end of the first member being positioned within the cavity such that the distal end of the first member engages the flange to prevent the first member from translating along the longitudinal axis in one direction.

5. A system as recited in claim 1, wherein the balloon is movable between a first configuration in which the balloon is twisted about the inner shaft and a second configuration in which the balloon is untwisted.

6. A system as recited in claim 1, wherein the first member comprises an inner surface defining a passageway and a flange, a distal end of the third member being positioned within the passageway such that the distal end of the third member engages the flange to prevent the third member from translating along the longitudinal axis in one direction to limit expansion of the balloon.

7. A system as recited in claim 1, wherein the second threaded surface extends from a shank of the second member, the shank being coupled to a head, the body comprising an inner surface defining a cavity, the second member being positioned within the cavity such that an outer surface of the head engages the inner surface.

8. A system as recited in claim 1, wherein the third member is rotatable relative to the first member to move the balloon between a first configuration in which the balloon is twisted about the inner shaft and a second configuration in which the balloon is untwisted.

9. A system as recited in claim 1, wherein the body comprises a slot, a pin extending through the slot and into the second member such that the pin moves within the slot along the longitudinal axis as the third member translates along the longitudinal axis.

10. A system as recited in claim 1, wherein the third member is rotatable relative to the first member to move the balloon between a first configuration in which the balloon is twisted about the inner shaft and has a first profile and a second configuration in which the balloon is untwisted and has a second profile that is greater than the first profile.

11. A system as recited in claim 1, further comprising a fourth member rotatably positioned within the body and an adapter coupled to the fourth member such that a proximal end of the adapter is fixed relative to the fourth member, the outer shaft being fixed to a distal end of a connector that is coupled to the adapter.

12. A system as recited in claim 11, wherein the proximal end of the adapter is positioned within a socket of the fourth member.

13. A system as recited in claim 11, wherein a distal end of the adapter comprises a valve and the proximal end of the adapter is rotated relative to the distal end of the adapter to open and close the valve about the inner shaft.

14. A system as recited in claim 11, wherein a distal end of the adapter comprises a valve and the proximal end of the adapter is rotated relative to the distal end of the adapter to move the valve between a first position in which the inner shaft is fixed relative to the outer shaft and a second position in which the inner shaft can translate relative to the outer shaft along the longitudinal axis.

15. A surgical system comprising:
a body extending along a longitudinal axis and comprising a cavity;
a collar comprising a distal end rotatably positioned within the cavity, the distal end comprising a threaded inner surface;
a bolt positioned within the cavity and comprising a threaded outer surface that engages the threaded inner surface, the bolt being non-rotatable relative to the body;
a stylet knob having a distal end positioned within the collar; and
an inflatable bone tamp comprising:
an outer shaft coupled to the body,
a balloon coupled to the outer shaft, and
an inner shaft having a proximal end that is fixed to the stylet knob and a distal end that is fixed to the balloon,
wherein the collar is rotatable relative to the body to translate the stylet knob along the longitudinal axis to control longitudinal growth of the balloon.

16. A system as recited in claim 15, wherein the balloon increases in length as the stylet knob translates along the longitudinal axis in a first direction and decreases in length as the stylet knob translates along the longitudinal axis in an opposite second direction.

17. A system as recited in claim 15, wherein the stylet knob is rotatable relative to the collar and a distal end of the balloon is fixed to the outer shaft such that rotating the stylet knob relative to the collar twists the balloon about the inner shaft.

18. A system as recited in claim 15, further comprising a second collar having a proximal end rotatably positioned within the cavity and an adapter coupled to a distal end of the second collar such that a proximal end of the adapter is fixed relative to the second collar, the outer shaft being fixed to a connector that is coupled to a distal end of the adapter.

19. A system as recited in claim 18, wherein the distal end of the adapter comprises a valve and the distal end of the second collar is rotatable relative to the body and the distal end of the adapter to move the valve between a first position in which the inner shaft is fixed relative to the outer shaft and a second position in which the inner shaft can translate relative to the outer shaft along the longitudinal axis.

20. A surgical system comprising:
a body extending along a longitudinal axis and comprising a cavity;
a collar comprising a distal end rotatably positioned within the cavity, the distal end comprising a threaded inner surface;
a stylet knob having a distal end positioned within a proximal end of the collar;
a bolt positioned within the cavity and comprising a threaded outer surface that engages the threaded inner surface;
a pin extending through a slot in the body and into the bolt to prevent rotation of the bolt relative to the body;
a second collar having a proximal end rotatably positioned within the cavity;
an adapter coupled to a distal end of the second collar such that a proximal end of the adapter is fixed relative to the second collar; and an inflatable bone tamp comprising:
- an outer shaft coupled to a distal end of a connector that engages the adapter,
- a balloon coupled to the outer shaft, and
- an inner shaft having a proximal end that engages the stylet knob and a distal end that engages an inner surface of the balloon to fix the inner shaft to the stylet knob and the balloon, wherein a distal end of the adapter comprises a valve and the distal end of the second collar is rotatable relative to the body and the distal end of the adapter to move the valve between a first position in which the inner shaft is fixed relative to the outer shaft and a second position in which the inner shaft can translate relative to the outer shaft along the longitudinal axis, and wherein the proximal end of the collar is rotatable relative to the body to translate the stylet knob along the longitudinal axis to alter a distance between a distal end of the outer shaft and a distal end of the inner shaft and control longitudinal growth of the balloon.

* * * * *